United States Patent
Fell

[11] Patent Number: 5,947,731
[45] Date of Patent: Sep. 7, 1999

[54] DENTAL TOOL FOR COMPOSITE TYPE FILLINGS AND METHOD OF USE THEREOF

[76] Inventor: William P. Fell, 549 W. Firewood Ln., Anch, Ak. 99503

[21] Appl. No.: 09/069,225

[22] Filed: Apr. 28, 1998

Related U.S. Application Data

[60] Provisional application No. 60/045,119, Apr. 30, 1997.
[51] Int. Cl.[6] ............................... A61C 3/13; B25B 7/12
[52] U.S. Cl. ............................................. 433/159; 81/302
[58] Field of Search .................... 433/4, 156, 157, 433/158, 159; 81/302

[56] References Cited

U.S. PATENT DOCUMENTS

| | | | |
|---|---|---|---|
| 315,706 | 4/1885 | Brewer et al. | 433/159 |
| 388,619 | 8/1888 | Booth | 433/159 |
| 390,561 | 10/1888 | Brown | 433/159 |
| 442,107 | 12/1890 | Davison | 433/159 |
| 1,349,767 | 8/1920 | Ivory | 433/159 |
| 1,438,975 | 12/1922 | Wiggins | 433/159 |
| 4,106,374 | 8/1978 | Dragan | 433/4 |

*Primary Examiner*—Ralph A. Lewis
*Attorney, Agent, or Firm*—Michael J. Tavella

[57] ABSTRACT

A dental tool for aiding in forming composite type dental fillings. The tool works by forcing the body of the tooth away from the contact surface on two surface (DO) class II posterior restorations, and by driving adjacent teeth away from contact on DO class II posterior restorations. The tool is a modified set of pliers in which the jaws push outwards when the handles are contracted. The jaws have small tips designed for the typical uses. One is a universal tip for MOD work. A second jaw is used for DO/MO left. The third is used for the DO/MO right.

17 Claims, 7 Drawing Sheets

DENTAL TOOL FOR COMPOSITE TYPE FILLINGS AND METHOD OF USE THEREOF

CROSS REFERENCE TO RELATED APPLICATIONS

This application claims benefit of U.S. Provisional Appl. 60/045,119, filed Apr. 30, 1997.

STATEMENT REGARDING FEDERALLY SPONSORED RESEARCH AND DEVELOPMENT

Not Applicable

BACKGROUND OF THE INVENTION

Field of the Invention

This invention is used in conjunction with standard tools for forming composite type dental fillings. Specifically, this tool is used for the creation of tight contacts of composite resin direct posterior restorations.

BRIEF SUMMARY OF THE INVENTION

This invention is used in conjunction with standard tools for forming composite type dental fillings. Specifically, this tool is used for the creation of tight contacts of composite resin direct posterior restorations. It works by forcing the body of the tooth away from the contact surface on two surface (DO) class II posterior restorations, and by driving adjacent teeth away from contact on DO class II posterior restorations. The force is maintained by either hand pressure or by a using a sliding collar on the tool's handles. The tool is a modified set of pliers in which the jaws push outwards when the handles are contracted. The jaws have small tips designed for the typical uses. One is a universal tip for MOD work. A second jaw is used for DO/MO left. The third is used for the DO/MO right. Tips are selected for the particular type of filling. The procedure for the use of the tool is the same.

The procedure for using this tool is as follows: After a tooth is prepared, a matrix and wedge of choice are put into position. The etching and surface bonding steps are performed as usual. The initial increment of direct posterior composite is placed into the proximal boxes of the preparation and then condensed into the marginal areas. Next, the tips of the tool (the proximal box probes) are placed into the unset composite in the proximal box portion of the preparation. While holding the probes firmly down into the unset composite, squeeze the handles of the tool. This forces the probes to displace the adjacent teeth away from the prepared tooth to compensate for the thickness of the matrix band. While holding the tool down, and squeezing the handles, the composite is "light cured". Once the composite is set, the probes are gently removed fro the set composite. Once the tool is removed, small voids are left. A thin coat of bonding resin is placed into the voids. Additional composite is incrementally placed until the area is filled. Once the composite is cured, the tooth is shaped and polished using standard techniques.

DETAILED DESCRIPTION OF THE INVENTION

Figure 1:
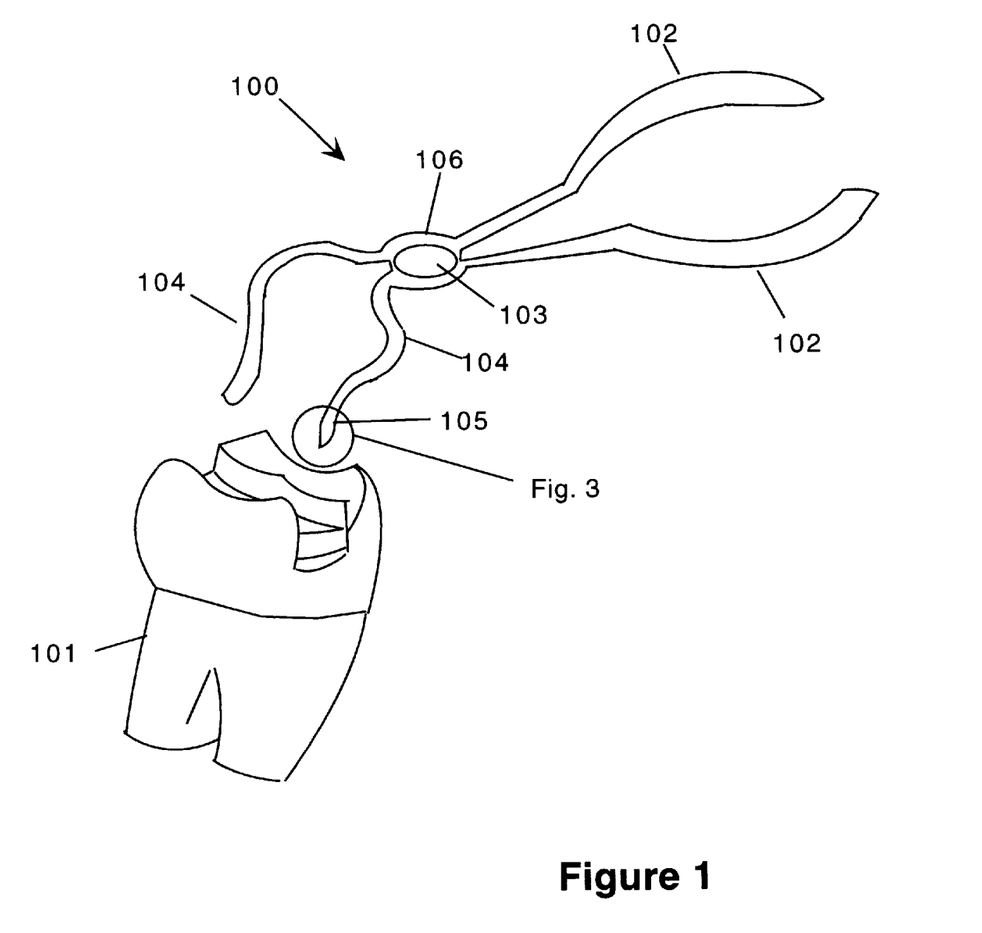
FIG. 1 is a perspective detail view of the tool ready for positioning on a tooth.
Figure 2:
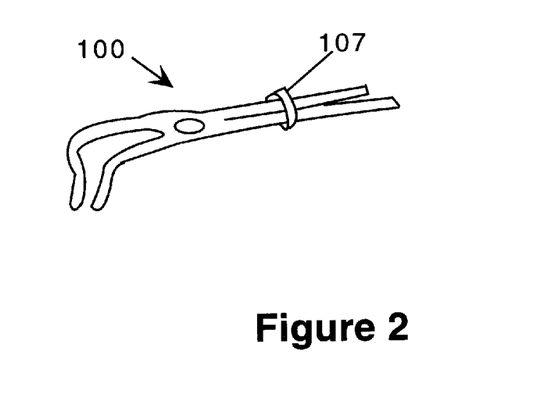
FIG. 2 is a perspective view of the tool showing a locking handle.
Figure 3:
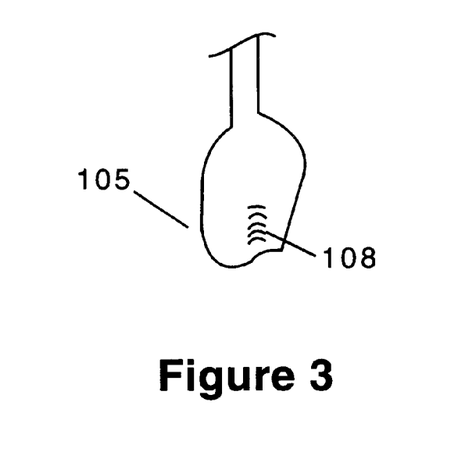
FIG. 3 is a perspective view of the contact end of the tool.
Figure 4:
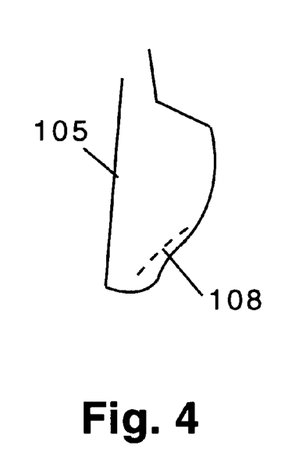
FIG. 4 is a side view of the contact end of the tool.
Figure 5:
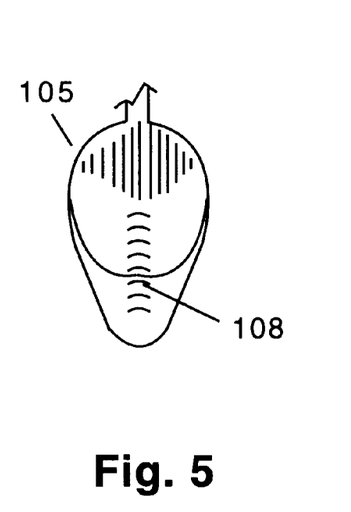
FIG. 5 is an inside view of the contact end of the tool.
Figure 6:
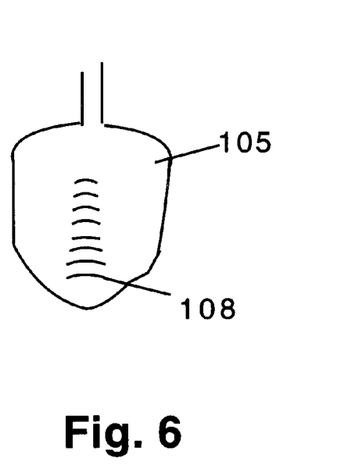
FIG. 6 is an outer view of the contact end of the tool.

FIG. 1 shows the tool 100 above a tooth 101. The tool 100 has two handles 102 that are joined by a hinge pin 103 (see, e.g., FIGS. 7, 8 and 9). A pair of contact arms 104 is provided. In the case of a single contact tool (e.g., FIG. 10) a single contact foot 105 is provided on one of the arms 104. The contact arms 104 are designed to spread apart when the handles 102 are squeezed. It is this action that works to spread teeth or a tooth during the composite filing process. To make holding the tool 100 easier, the handles can be fitted with a ratchet 106 or with a clamp 107 (see FIG. 2). It is important to provide adequate pressure on the arms 104 during the filling process. FIG. 3 shows a perspective view of a contact foot 105. This foot 105 has a number of grooves 108 formed on the outer surface. The groove is for composite from the gingival floor. FIG. 4 is a side view of the foot 105. FIG. 5 is a view of the inside of the contact foot 105 and FIG. 6 is a view of the outside of the foot 105.

Figure 7:
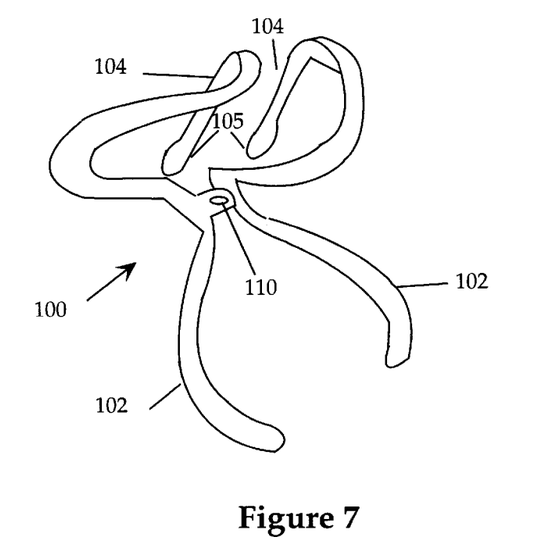
FIG. 7 is a top rear perspective view of the tool showing the curved handles.
Figure 8:
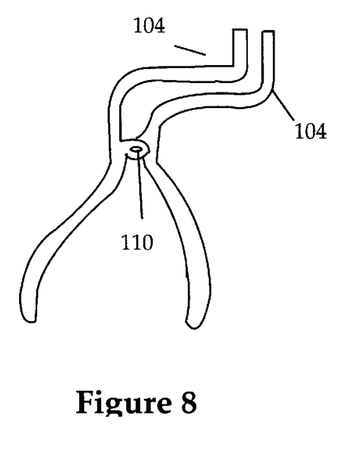
FIG. 8 is a perspective view of the tool showing the pivoting hinge.
Figure 9:
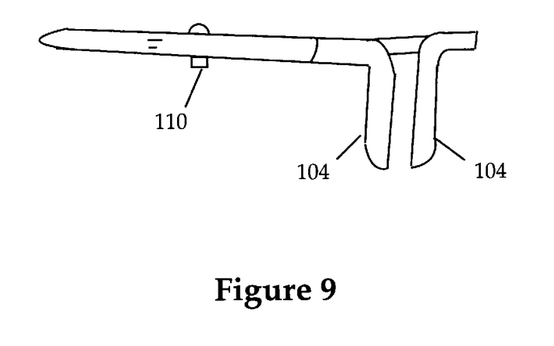
FIG. 9 is a side view of the tool.

FIGS. 7–9 show various views of the tool 100. The hinge point 110 is shown in all views. Note that, as mentioned above, moving the handles 102 inward causes the contact forming arms 104 to move outward.

Figure 10:
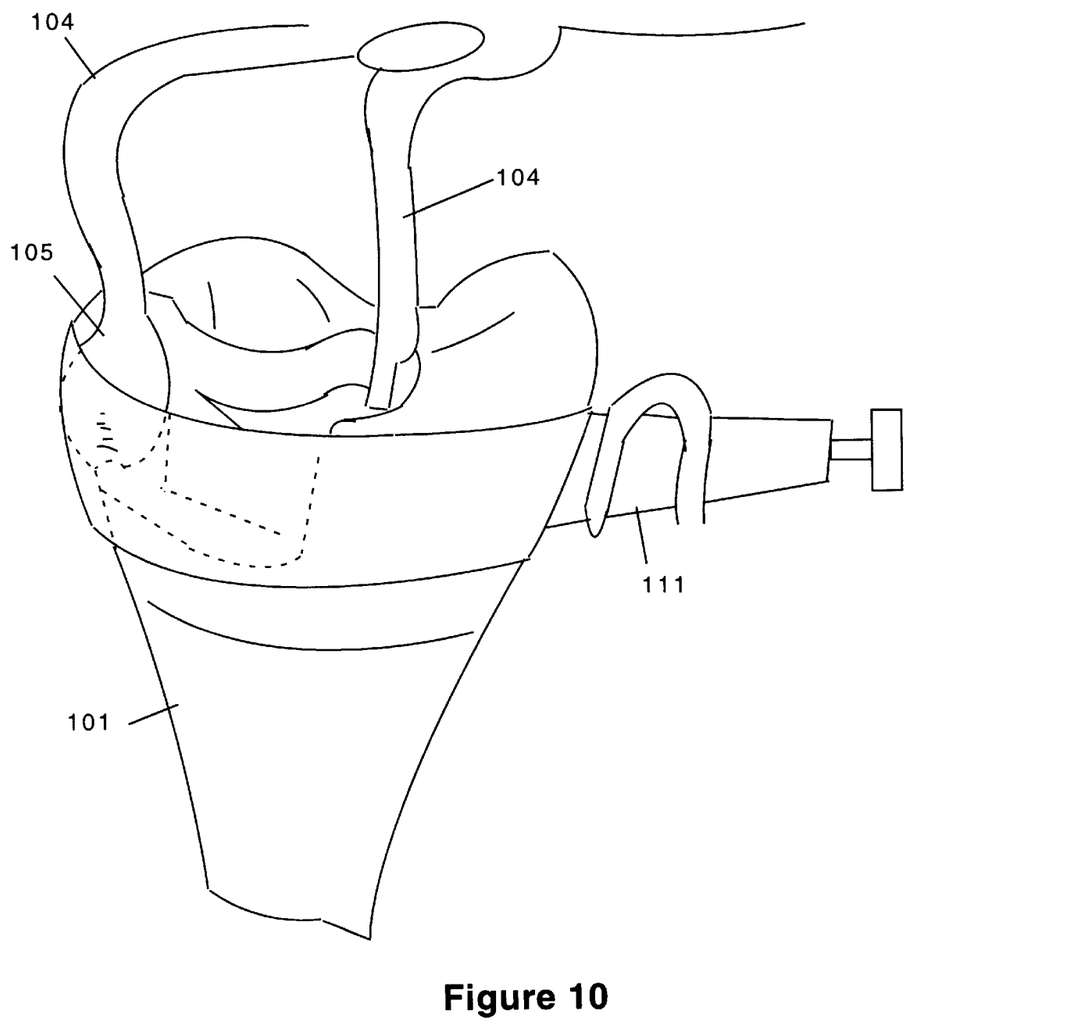
FIG. 10 is a detail view of a single contact tool in place on a tooth.
Figure 11:
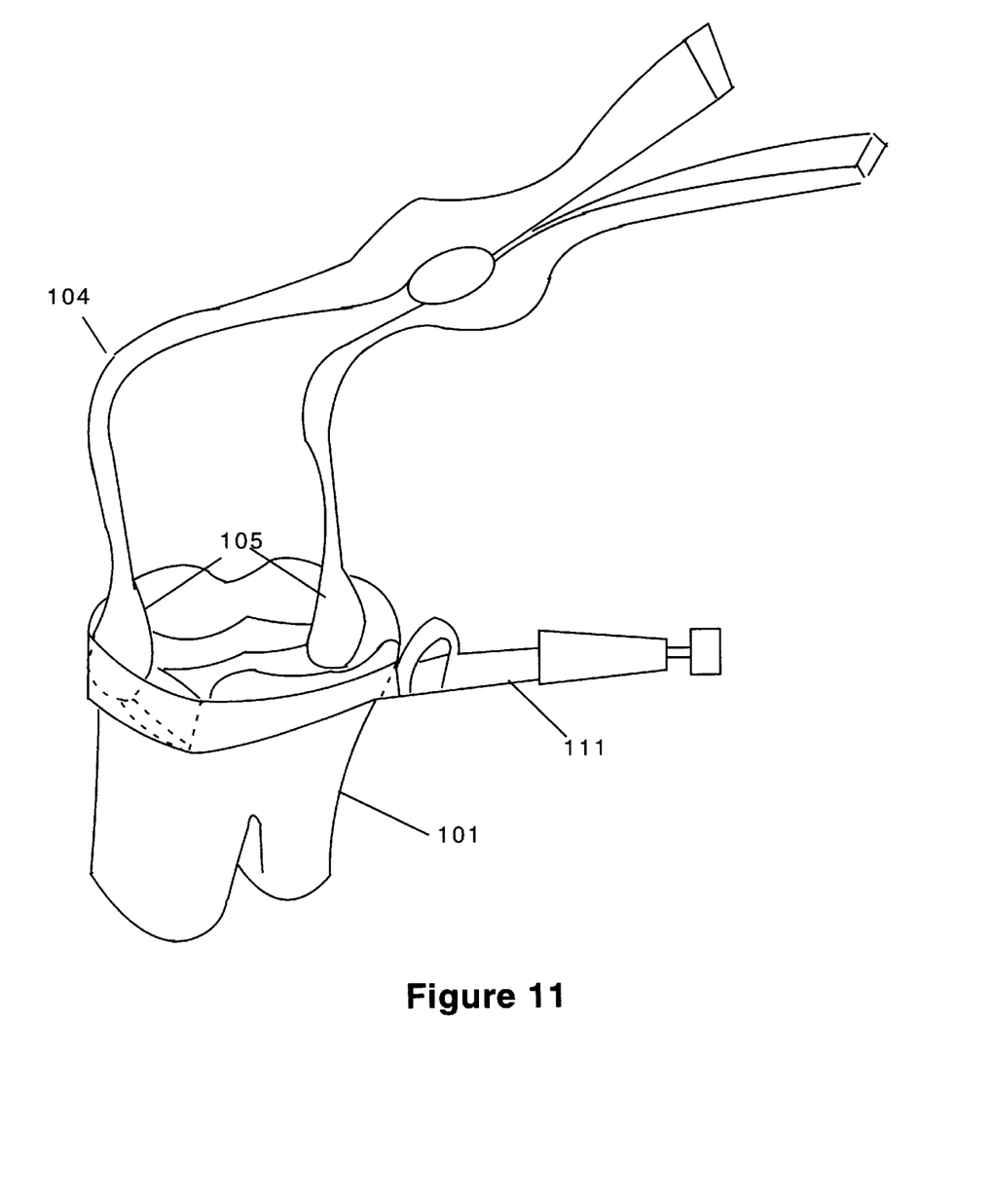
FIG. 11 is a detail view of a double contact tool in place on a tooth.

FIG. 10 shows a single point tool 100 in place on a tooth during a composite filling. A standard matrix retainer 111 is in place on the tooth 101. The tool 100 is placed as shown. The tool 100 then forces open the space for the composite filling by pushing against the retainer and the tooth body. FIG. 11 shows a tool 100 that has a pair of contact feet 105.

Figure 12:
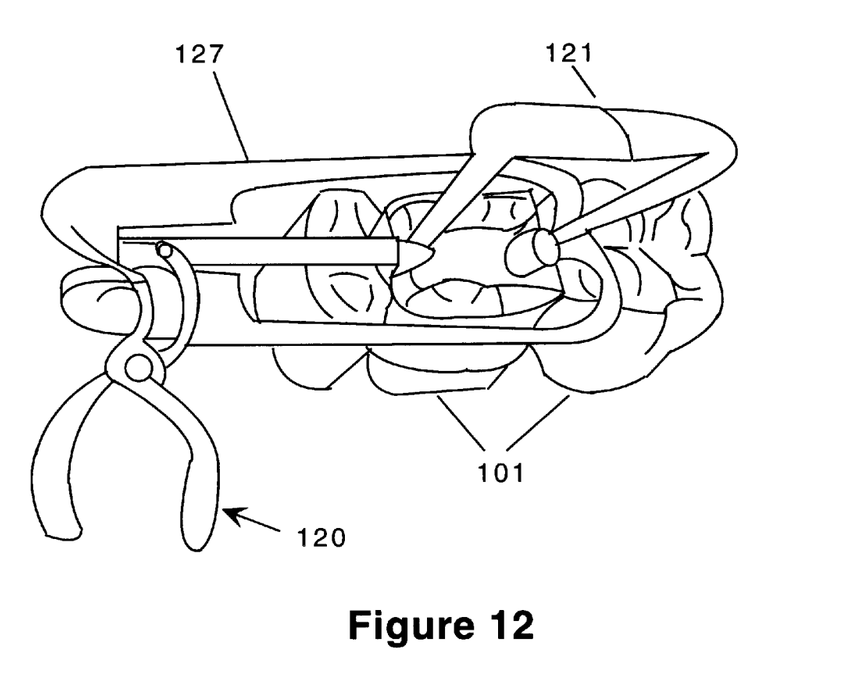
FIG. 12 is a detail view of a second embodiment of the tool.
Figure 13:
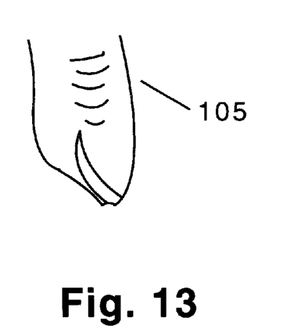
FIG. 13 is a detail of a contact point.
Figure 14:
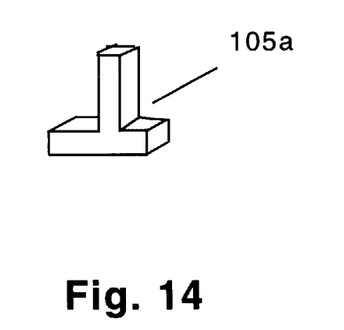
FIG. 14 is a detail of a "T" joint.
Figure 15:
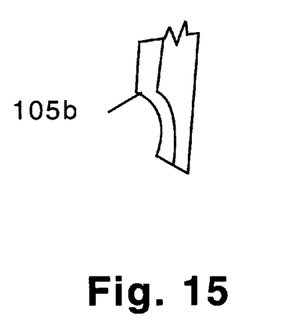
FIG. 15 is a detail view of a sharp point contact point.

FIG. 12 shows a second embodiment 120 of the tool. This embodiment is designed to force a space between adjacent teeth during the filing process. This tool has a pair of contact arms 104 that are connected to a retainer wall 127, which fits around a set of teeth. This model has removable contact points to allow varying setups. For example, one set up uses a contact forming surface 105 (FIG. 13) one end of the contact arms and either a "T" joint 105a (FIG. 14) or a sharp point 105b (FIG. 15) on the other control arm to gain a purchase point for resistance force against the contact making side.

Figure 16:
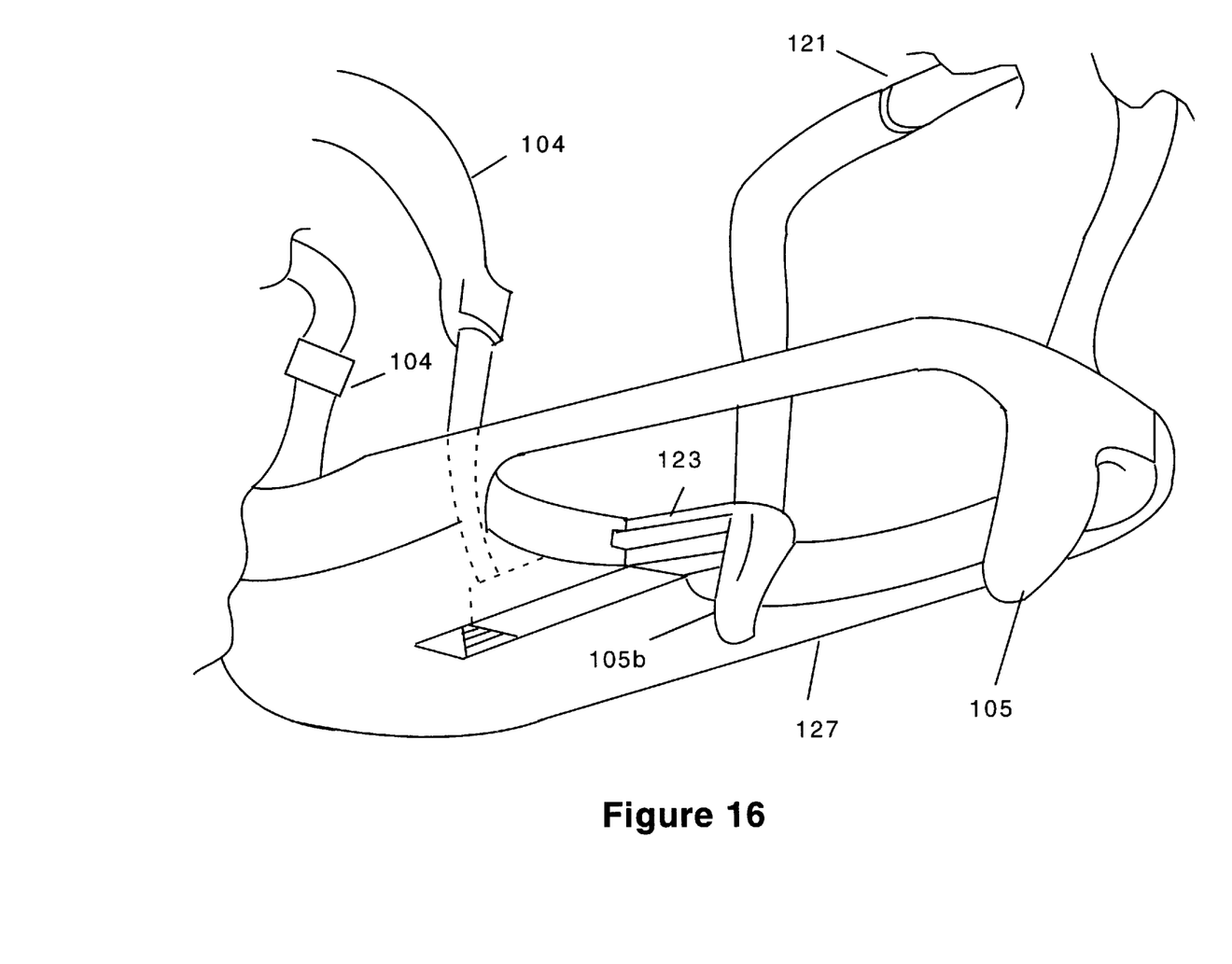
FIG. 16 is an enlarged perspective view of the second embodiment of the tool.

FIG. 16 is an enlarged view of the tool 120. To make initial adjustments, a finger pressure slide 121 and a sliding slot contact former 123 are used to set the tool 120 in place over the teeth. Once the tool 120 is in position, the handles 102 are used to apply the desired pressure on the teeth.

The procedure for using these tools is as follows: After a tooth is prepared, a matrix and wedge of choice are put into position. The etching and surface bonding steps are performed as usual. The initial increment of direct posterior composite is placed into the proximal boxes of the preparation and then condensed into the marginal areas. Next, the tips of the tool (the proximal box probes) are placed into the unset composite in the proximal box portion of the preparation. While holding the probes firmly down into the unset composite, squeeze the handles of the tool. This forces the probes to displace the adjacent teeth away from the prepared tooth to compensate for the thickness of the matrix band. While holding the tool down, and squeezing the handles, the composite is "light cured". Once the composite is set, the probes are gently removed fro the set composite. Once the tool is removed, small voids are left. A thin coat of bonding resin is placed into the voids. Additional composite is incrementally placed until the area is filled. Once the composite is cured, the tooth is shaped and polished using standard techniques.

The present disclosure should not be construed in any limited sense other than that limited by the scope of the claims having regard to the teachings herein and the prior art being apparent with the preferred form of the invention disclosed herein and which reveals details of structure of a preferred form necessary for a better understanding of the invention and may be subject to change by skilled persons within the scope of the invention without departing from the concept thereof.

I claim:

1. A dental tool for composite type fillings comprising:
   a) a pair of elongated members, each elongated member having a first end and a second end, the first end of said pair of elongated members being a handle end and the second end of said pair of elongated members being a jaw end, said pair of elongated members being pivotably connected together between their ends such that when said handle end is squeezed inwardly, said jaw end is forced outward with respect to said handle end; and
   b) at least one contact foot, fixedly attached to the second end of one of said elongated members, said contact foot has a smooth curved front face and a concave back face, said contact foot also being tapered downwardly from said second end, said contact foot also having a plurality of grooves formed on said concave back face.

2. The dental tool of claim 1 further comprising a second contact foot, fixedly attached to the second end of the other elongated member, said second contact foot having a smooth curved front face and a concave back face, said contact foot also being tapered downwardly from said jaw end, said contact foot also having a plurality of grooves formed on said concave back face.

3. The dental tool of claim 1 further comprising a spacer foot, fixedly attached to the second end of the other elongated member, said spacer foot being used to obtain a purchase for applying pressure with the dental tool.

4. The dental tool of claim 3 wherein the spacer foot is a "Tee" shaped member.

5. The dental tool of claim 3 wherein the spacer foot is a tapered member.

6. A dental tool for composite type fillings comprising:
   a) a pair of elongated members, each elongated member having a first end and a second end, the first end of said pair of elongated members being a handle end and the second end of said pair of elongated members being a jaw end, said pair of elongated members being pivotably connected between their ends such that when said handle end is squeezed inwardly, said jaw end is forced outward with respect to said handle end;
   b) a means for receiving and holding a foot, formed in the second ends of said pair of elongated members; and
   c) at least one contact foot, removably attached to one of the means for receiving and holding a foot, said contact foot having a smooth curved front face and a concave back face, said contact foot also being tapered downwardly from said second end, said contact foot also having a plurality of grooves formed on said concave back face.

7. The dental tool of claim 6 further comprising a second contact foot, removably attached to the means for receiving and holding a foot in said second end of the other elongated member, said second contact foot having a smooth curved front face and a concave back face, said contact foot also being tapered downwardly from said jaw end, said contact foot also having a plurality of grooves formed on said concave back face.

8. The dental tool of claim 6 further comprising a spacer foot, removably attached to the means for receiving and holding a foot in said second end of the other elongated member, said spacer foot being used to obtain a purchase for applying pressure with the dental tool.

9. The dental tool of claim 8 wherein the spacer foot is a "Tee" shaped member.

10. The dental tool of claim 8 wherein the spacer foot is a tapered member.

11. A method of forming a composite type dental filling using a dental tool having a pair of elongated members, each elongated member having a first end and a second end, the first end of said pair of elongated members being a handle end and the second end of said pair of elongated members being a jaw end,:
    a) preparing a tooth for a composite type filling;
    b) placing a matrix band;
    c) applying an initial increment of a composite material into proximal boxes of the prepared tooth;
    d) condensing the composite material into marginal areas of said prepared tooth;
    e) placing the jaw ends of the dental tool into the unset composite material in the proximal box portion of the prepared tooth;
    f) holding the tool firmly down into the unset composite material;
    g) squeezing the handles of the tool, thereby forcing the jaw ends to displace adjacent teeth away from the prepared tooth to compensate for the thickness of the matrix band;
    h) curing the composite material; and
    i) removing the dental tool.

12. The method of claim 11 further comprising the steps of:
    a) filling small voids created by the jaw ends of the dental tool with a thin coat of bonding resin;
    b) adding additional composite material until the area is filled;
    c) curing the additional composite material;
    d) shaping the composite material; and
    e) polishing the composite material.

13. The method of claim 11 wherein the jaw end of said dental tool has at least one contact foot attached to said jaw end, said contact foot has a smooth curved front face and a concave back face, said contact foot also being tapered downwardly from said jaw end, said contact foot also having a plurality of grooves formed on said concave back face.

14. The method of claim 13 wherein the dental tool further comprises a second contact foot, fixedly attached to the jaw end, said second contact foot having a smooth curved front face and a concave back face, said contact foot also being tapered downwardly from said jaw end, said contact foot also having a plurality of grooves formed on said concave back face.

15. The method of claim 13 wherein the dental tool further comprises a spacer foot, attached to the jaw end, said spacer foot being used to obtain a purchase for applying pressure with the dental tool.

16. The method of claim 15 wherein the spacer foot is a "Tee" shaped member.

17. The dental tool of claim 15 wherein the spacer foot is a tapered member.

* * * * *